: US 10,357,624 B2
(12) United States Patent
Van Der Staay et al.

(10) Patent No.: US 10,357,624 B2
(45) Date of Patent: Jul. 23, 2019

(54) VENTILATOR APPARATUS AND METHOD FOR OPERATING A VENTILATOR IN SAID VENTILATOR APPARATUS

(71) Applicant: iAsset ag, Buchs SG (CH)

(72) Inventors: Matthias Van Der Staay, Gossau ZH (CH); Harri Friberg, Mauren (LI)

(73) Assignee: iAsset ag, Buchs SG (CH)

( * ) Notice: Subject to any disclaimer, the term of this patent is extended or adjusted under 35 U.S.C. 154(b) by 420 days.

(21) Appl. No.: 15/370,255

(22) Filed: Dec. 6, 2016

(65) Prior Publication Data

US 2018/0154095 A1 Jun. 7, 2018

(51) Int. Cl.
*A61M 16/00* (2006.01)
*G16H 50/50* (2018.01)
(Continued)

(52) U.S. Cl.
CPC .... *A61M 16/0051* (2013.01); *A61M 16/0069* (2014.02); *A61M 16/024* (2017.08); *G16H 20/40* (2018.01); *G16H 50/50* (2018.01); *A61M 2016/0021* (2013.01); *A61M 2016/0027* (2013.01); *A61M 2016/0036* (2013.01);
(Continued)

(58) Field of Classification Search
CPC .. A61M 2016/0015; A61M 2016/0027; A61M 2016/003; A61M 2016/102; A61M 2205/33
See application file for complete search history.

(56) References Cited

U.S. PATENT DOCUMENTS

2005/0109340 A1* 5/2005 Tehrani ............... A61M 16/026
128/204.21
2011/0041850 A1 2/2011 Vandine et al.

FOREIGN PATENT DOCUMENTS

CA 2651287 A1 7/2010
GB 2472116 A 1/2011
(Continued)

OTHER PUBLICATIONS

Otis A B et al: "Mechanics of breathing in man.", Journal of Applied Physiology, vol. 2, No. 11, May 1, 1950 (May 1, 1950), pp. 592-607, XP002780255, ISSN: 0021-8987, DOI: 10.1152 / jappl . 1950. 2.11.592; the whole document.

*Primary Examiner* — Edelmira Bosques
(74) *Attorney, Agent, or Firm* — Nadya Reingand; Yan Hankin

(57) ABSTRACT

The invention comprises a ventilation apparatus and method for operating a ventilator of a ventilator apparatus, wherein in the method at least one duration ratio factor is set in a computing system of the ventilator apparatus; at least one minute volume, at least one functional dead space volume and at least one time constant are determined; a respiration frequency is computed, based on a previously defined lung model, depending on said determined parameters, where said computed respiration frequency is optimized on at least one minimum of a delivered parameter, which is induced to a patient using said ventilator; an inspiratory time and an expiratory time are determined based on said computed respiration frequency and said duration ratio factor; at least one tidal volume based on said previously computed respiration frequency and said determined minute volume is computed; and a delivered respiratory parameter of the ventilator is closed loop controlled.

22 Claims, 6 Drawing Sheets

(51) Int. Cl.
  *G16H 20/40* (2018.01)
  *A61M 16/10* (2006.01)
(52) U.S. Cl.
  CPC .............. *A61M 2016/1025* (2013.01); *A61M 2205/3303* (2013.01); *A61M 2205/3344* (2013.01); *A61M 2205/50* (2013.01); *A61M 2205/505* (2013.01); *A61M 2230/432* (2013.01); *A61M 2230/435* (2013.01); *A61M 2230/46* (2013.01)

(56) References Cited

FOREIGN PATENT DOCUMENTS

| | | |
|---|---|---|
| WO | 2011089491 A1 | 7/2011 |
| WO | 2016037627 A1 | 3/2016 |

\* cited by examiner

(ARDS patient):
R = 9 mbar/l/s
C = 25 ml/mbar
IBW = 70kg
Vd/kg = 2.2ml/kg

VENTILATOR APPARATUS AND METHOD FOR OPERATING A VENTILATOR IN SAID VENTILATOR APPARATUS

FIELD OF THE INVENTION

The invention relates to a ventilator apparatus and a method for operating a ventilator in a ventilator apparatus. More particularly, the present invention relates to ventilator apparatus, or breathing apparatus, and a method for operating a ventilator in a ventilator apparatus based on an optimized delivered respiration parameter from the ventilator of the ventilator apparatus to the patient.

BACKGROUND OF THE INVENTION

Patients who have certain respiratory disease for different medical reasons or who have to undergo surgery must be provided with artificial respiration. A modern mechanical ventilator apparatus for a patient should be adapted to provide sufficient oxygenation and sufficient ventilation for the patient's lung.

In the recent years, a ventilation apparatus has been developed to support the patient respiration and to improve the patients comfort. Therefore, a variety of ventilation modes have been developed that can potentially avoid complications and thus shorten the duration of medical ventilations. One example is the pressure controlled ventilation (PCV), where the ventilator delivers a flow to maintain a set pressure at a present respiratory rate over a present inspiratory time.

Mammals, in particular humans, need a minimum amount of gas exchange in their lung to breath without any technical support, which mainly depends on the alveolar minute volume (Mva). The alveolar minute volume (Mva) is the alveolar volume of gas inhaled or exhaled from a human per minute and is calculated by a respiratory frequency (f) and an alveolar tidal volume (Vta). In 1950 Otis et. al described the mechanical work, done by the human respiratory muscles to produce the movements of breathing, follows the minimum work of breathing triggered by the respiratory muscles. Concerning the assumption that humans breathe spontaneously, without any technical support, Otis et. al found the following correlation between a respiratory frequency (f) and the alveolar minute volume (Mva):

$$f = \frac{\sqrt{1 + 4*\pi^2*R*C*\frac{Mva}{Vd}} - 1}{2*\pi^2*R*C}, \quad \text{(Eq. 1)}$$

where R is the airway resistance and C is the lung compliance and Vd is the functional dead volume. This correlation is the fundament of one of the mostly used modern ventilation mode for mechanical ventilation—the adaptive support ventilation (ASV) mode. The adaptive support ventilation (ASV) mode was developed by F. Tehrani, who adapted the equation of Otis et. al and modified it with the following substitution, $$Mva = Mvp - Vd * f, \quad \text{(Eq. 2)}$$

where Mvp is the proximal minute volume, Vd is the functional dead space and f is the respiratory frequency. The resulting respiratory frequency (f) in the ASV mode represents the frequency with which a human being would breathe naturally.

U.S. Pat. No. 4,986,268 A shows a method and an apparatus for automatically controlling a respirator. A software algorithm is used to compute the amount and optimum frequency of ventilation required for the next required breath of the patient. Said frequency of ventilation is calculated based on the minimum work of breathing of the patient and controls said apparatus.

U.S. Pat. No. 8,695,593 B2 shows a method of providing treatment advice for patients on mechanical ventilation. It provides advice on how much ventilation a patient requires and recommends ventilator settings to minimize the respiration work rate based on the ASV mode.

However, the previously described techniques were developed for a specific group of patients. The ASV mode, based on Otis et. al, uses a spontaneously breathing and a non-supported patient as reference. That is, particularly for mandatory ventilation, wrong and for pressure supported ventilation not exactly the same. The pressure course of mandatory breaths as well as pressure supported breaths can be approximated by a rectangular function, while the pressure course of non-supported breaths is more equal to a sine curve. This mismatch results into an increased stress for the patient's lung. Especially, patients with restrictive lung disease, like acute respiratory distress syndrome (ARDS) or Fibrosis must be ventilated with a more protective ventilation mode. Insufficient assistance includes diaphragmatic fatigue or weakness and force the recruitment of accessory inspiration muscles, sometimes leading to respiratory acidosis.

SUMMARY OF THE INVENTION

There is a need to give an enhanced artificial respiration to a patient, which protects the lungs of the patient during ventilation and is suitable for every patient, independent of a presence of a spontaneous breathing of the patient.

This need is solved by means of the subject matters with the features according to the independent patent claims. Further exemplary embodiments are shown in the dependent claims.

According to an exemplary embodiment of the present invention, a method for operating a ventilator in a ventilator apparatus, wherein in the method at least one duration ratio factor (D1, D2) is set in a computing system of the ventilator apparatus (step a); at least one minute volume (Mv) is determined using said computing system (step b); at least one functional dead space volume (Vd) is determined using said computing system (step c); at least one time constant (R*C) is determined using said computing system (step d); a respiration frequency (f) is computed using said computing system, based on a previously defined lung model (LM), depending on said determined minute volume (Mv), said determined functional dead space (Vd), said determined time constant (R*C) and said set duration ratio factor (D1, D2), where said computed respiration frequency (f) is optimized on at least one minimum of a delivered parameter (G_tot), which is induced to a patient using said ventilator (step e); an inspiratory time (Ti) and an expiratory time (Te) are determined based on said computed respiration frequency (f) and said duration ratio factor (D1, D2) using said computing system (step f); at least one tidal volume (Vt) based on said previously computed respiration frequency (f) and said determined minute volume (Mv) is computed using said computing system (step g); and at least one of a delivered respiratory parameter of the ventilator including at least one of a respiratory pressure (Rp), a respiratory flow (Rf) or a respiratory volume (Rv) is closed loop controlled based on the steps e) to g) (step h). Thereby, the respiratory parameter delivered from said ventilator apparatus to the lung of the patient is optimized in an improved manner, while the tidal volume (Vt) is lowered and the respiration pressure (Rp) imposed to the lungs of the patient is lowered during a continuous ventilation of the patient.

After starting with step a), the sequence of step b) to step d) are ordered randomly, while the sequence of step e) to step g) are mandatory. The present method is suitable for any kind of patients, while an active patient is able to breath spontaneously and an inactive patient is not able to breath spontaneously. Said computed respiration frequency (f) is computed iteratively in said computing system and is used to adjust at least one respiration parameter of the patient, including the proximal respiration pressure (Rpp) or the proximal respiration flow (Rfp) of the patient according to a continuously ventilation of the patient. Thereby, said respiration frequency (f) is used to compute said at least one respiration parameter very accurate. Said time constant (R*C) is determined during the continuously measurement of at least one respiration parameter of the patient including at least one of the proximal respiration pressure (Rpp) or the proximal respiration flow (Rfp) of the patient. Thereby a quick determination of the time constant (R*C) is ensured.

According to a further embodiment of the present invention, wherein in the method said at least one delivered respiratory parameter of the ventilator apparatus is cascaded closed loop controlled. For example, by closed loop controlling said tidal volume (Vt) in a first cascade and closed loop controlling said delivered respiratory pressure (Rp) in a second cascade by using a cascaded closed loop controller. This leads to an enhanced closed loop controlling in the ventilation apparatus and further to an enhanced respiration of the patient.

According to an exemplary embodiment of the present invention, wherein in the method said steps b) to g) are repeated at least once and subsequently step h) is performed. Thereby, said computed respiration frequency (f) and said tidal volume (Vt) are determined more accurate, which results to an improved operation of the ventilator in the ventilator apparatus and furthermore leads to an enhanced ventilation of the lungs of the patient.

According to a further exemplary embodiment of the present invention, wherein said at least one minimum of a delivered parameter (G_tot), includes at least one minimum of the delivered mechanical respiration mean power ($\dot{W}$_tot), which is induced to the patient using at least one actuator of said ventilator. This results in an increased computed respiration frequency (f), which leads to a protective ventilation for the lungs of the patient.

According to an exemplary embodiment of the present invention, wherein in the method said lung model (LM) in step e) comprises an airway resistance (R) and a lung compliance (C), which following at least a linear behavior or at least a quadratic behavior or at least a polynomial behavior. Therefore, the airways resistance (R) and the lung compliance (C) can be treated independently and determined very accurately in the computing system, while different complex lung models are used. This leads to a very accurate improvement of the operation of said ventilator, with an enhanced working point in said ventilator of the ventilator apparatus.

According to a further exemplary embodiment of the present invention, wherein in the method said lung model (LM) in step e) comprises at least one of the group of an assumed respiratory pressure (Rp_id), an assumed respiratory flow (Rf_id) and an assumed respiratory volume (Rv_id), which following at least one of an exponential behavior, a rectangular behavior, a sinusoidal behavior or a saw tooth behavior, which leads to a very accurate lung model (LM) and finally an enhanced mechanical ventilation of the patient. The choice of the behavior of the assumed respiratory parameters is advantageous for different kinds of patients and depends on the patient's respiration requirements. For example, patients with restrictive lung disease, like acute respiratory distress syndrome (ARDS) can be ventilated very gently, if a rectangular behavior of the respiratory pressure (Rp_id) is used.

According to an exemplary embodiment of the present invention, wherein in the method said minute volume (Mv) in step b) is the proximal minute volume (Mvp) calculated based on a previously determined patient's ideal body weight (IBW) and a previously determined percentage proximal minute volume (% Mvp), which is provided to said computing system using a user interface of the ventilator apparatus. This leads to a user-friendly handling for the user.

According to a further exemplary embodiment of the present invention, wherein in the method said minute volume (Mv) in step b) is the alveolar minute volume (Mva), which is provided to said computing system using a user interface of the ventilator apparatus. Therefore, the computed tidal volume (Vt) in step g) has to consider additionally the dead space (Vd) during computation. This enables an easy and quick strategy for setting up the amount of ventilation, which is important in case of an emergency.

According to an exemplary embodiment of the present invention, wherein in the method said minute volume (Mv) in step b) is the alveolar minute volume (Mva), which is determined based on a carbon dioxide content measurement in the patient's blood or in the patient's respiratory gas. This enables a different and flexible strategy for setting up the amount of ventilation.

According to a further exemplary embodiment of the present invention, wherein in the method said computed respiration frequency (f) in step e), which is optimized on at least one minimum of a delivered parameter (G_tot), which is induced to the patient using said ventilator, additionally depending on a positive end-expiratory pressure (PEEP). Therefore, the preferred working point of said ventilator will be reached more accurately.

According to an exemplary embodiment of the present invention, wherein in the method said positive end-expiratory pressure (PEEP), is a received input data of the computing system of the ventilator apparatus, which leads to a quick data processing and therefore to an enhanced artificial respiration of the patient.

According to a further exemplary embodiment of the present invention, wherein in the method said determined functional dead space (Vd) (step c) is determined based on a carbon dioxide measurement (DCO2), which leads to a more accurate computation of the respiration frequency (f) and the tidal volume (Vt) and therefore to an enhanced protection of the patient's lung.

According to an exemplary embodiment of the present invention, wherein in the method said determined functional dead space (Vd) (step c) is determined based on the patient's ideal body weight (IBW) multiplied by the usually used factor of 2.2 ml/kg. This leads to a quick and easy estimation of the functional dead space (Vd).

According to a further exemplary embodiment of the present invention, wherein in the method said determined functional dead space (Vd) (step c) is determined based on volumetric capnography, measured with a carbon dioxide measurement (DCO2) and proximal flow measurement. This leads to a very accurate determination of the functional dead space (Vd). There are several other measurement methods to determine the carbon dioxide data, which can be used for the determination of the functional dead space (Vd). According to an exemplary embodiment of the present invention, wherein in the method said computed respiration frequency (f) in step e) is optimized on at least one minimum of the delivered mechanical respiration work (W_tot), which is induced to the patient using said at least one actuator of said ventilator. Thereby an improvement of the operation of said ventilator is given and therefore a protective ventilation of the patient's lung is ensured.

According to a further exemplary embodiment of the present invention, wherein in the method a set first duration ratio factor (D1) in step a) is computed with said computing system by:

$$D1 = \frac{I:E}{(1+I:E)}, \quad \text{(Eq. 3)}$$

where I:E is the inspiration-to-expiration ratio and said first duration ratio factor (D1) is used for computing said respiration frequency (f) in step e). This leads to a very quick determination of the first duration ratio factor (D1).

According to an exemplary embodiment of the present invention, wherein in the method said first duration ratio factor (D1) in step a) is set to a value between 0.5 and 0.3 and is used for computing said respiration frequency (f) with said computing system in step e). This leads to a sufficient inspiration and expiration for the patient, which is accepted in the technical field of clinical ventilation.

According to a further exemplary embodiment of the present invention, wherein in the method said first duration ratio factor (D1) in step a) is about 0.36 and is used for computing said respiration frequency (f) with said computing system in step e). This leads to an optimal inspiration and expiration for the patient and a higher acceptance in the technical field of clinical ventilation.

According to an exemplary embodiment of the present invention, wherein in the method a set first duration ratio factor (D1) in step a) is set to a value of 0.5 and is used for the iteratively computing the respiration frequency (f) with said computing system in step e). This leads to an ideal inspiration and expiration for the patient.

According to a further exemplary embodiment of the present invention, wherein in the method a second duration ratio factor (D2), which is additionally set in step a) is used to determine said inspiration time (Ti) and said expiration time (Te) in step f) and is unequal to said first duration ratio factor (D1). This leads to an enhanced solution to compute said inspiration time (Ti) and said expiration time (Te) in said computing system.

According to a further exemplary embodiment of the present invention, wherein in the method a second duration ratio factor (D2), which is additionally set in step a) is used to determine said inspiration time (Ti) and said expiration time (Te) in step f) and is determined by an inspiration-to-expiration (I:E) ratio. This leads to a very quick determination of, the first duration factor (D1) and a quick method to compute said inspiration time (Ti) and said expiration time (Te) in said computing system.

According to an exemplary embodiment of the present invention, wherein in the method a second duration ratio factor (D2), which is additionally set in step a) is set to a value of 0.5. This leads to a very accurate solution to compute said inspiration time (Ti) and said expiration time (Te), which results in a preferable oxygenation.

According to a further exemplary embodiment of the present invention, wherein in the method said inspiration time (Ti) is limited by an extremum, in particular said maximum and said minimum. Therefore, a protective artificial respiration of the patient is ensured.

According to an exemplary embodiment of the present invention, wherein in the method said inspiration time (Ti) is limited by an extremum, in particular a minimum value computed with said computing system as:

$$\max(R^*C, 0.5s), \quad \text{(Eq. 4)}$$

Where R*C is a time constant in seconds. Therefore, a safe and lung protective lung ventilation of the patient is ensured.

According to a further exemplary embodiment of the present invention, wherein in the method said inspiration time (Ti) is limited by an extremum, in particular depending on a maximum value computed with said computing system as:

$$\max(Ti_{max\_IBW}, \min(Ti_{max}, 3^*R^*C)), \quad \text{(Eq. 5)}$$

where $Ti_{max\_IBW}$ is a maximum inspiration time based on the ideal body weight of the patient, which comprises a range of 1 second to 3 seconds, $Ti_{max}$ is a maximum inspiration time, which comprises a range of 2 seconds and 3 seconds, R*C is the time constant in seconds. Therefore, a safe and lung protective lung ventilation of the patient is ensured.

According to an exemplary embodiment of the present invention, wherein in the method the step d) further comprises determining at least one lung compliance (C) using said computing system, which leads to a very accurate determination of the respiration time limits.

According to a further exemplary embodiment of the present invention, wherein in the method said expiration time (Te) is limited by an extremum, in particular said maximum and said minimum. Therefore, a safe and lung protective ventilation of the patient is ensured.

According to an exemplary embodiment of the present invention, wherein in the method said expiration time (Te) is limited by an extremum, in particular a minimum value computed with said computing system as:

$$R*C*\max\left(2, \ln\left(\frac{Vt}{C*PEEP_{intr}}+1\right)\right), \quad \text{(Eq. 6)}$$

where R*C is a time constant in seconds, Vt is the tidal volume and $PEEP_{intr}$ is the upper limit for the intrinsic positive end-expiratory pressure. Therefore, a safe and lung protective lung ventilation of the patient is ensured.

According to a further exemplary embodiment of the present invention, wherein in the method said upper limit for the intrinsic positive end-expiratory pressure ($PEEP_{intr}$) is set to a value of 1.5 mbar, which leads to a quick computation of said expiration time (Te).

According to an exemplary embodiment of the present invention, wherein in the method said expiration time (Te) is limited with a maximum value less than 13 seconds, which leads to a safe operation of the ventilator apparatus.

According to a further exemplary embodiment of the present invention, wherein in the method after the step d) a percentage of spontaneous breaths of a patient (% Support) is determined by a proximal pressure and a proximal flow measured with at least one transducer of said ventilator apparatus, which leads to an improved respiratory diagnostic of the patient.

According to an exemplary embodiment of the present invention, wherein in the method said computed respiration frequency (f) of said ventilator apparatus is further optimized based on said percentage of spontaneous breaths of the patient (% Support) using said computing system. Therefore, weaning of the patient from the ventilator apparatus is enhanced.

According to a further exemplary embodiment of the present invention, wherein in the method said optimization of said computed respiration frequency (f) is delayed in case of a change from lower respiration frequencies to higher respiration frequencies, which leads to an enhancement of the weaning of the patient.

According to an exemplary embodiment of the present invention, wherein in the method said optimization of said computed respiration frequency (f) is delayed in case of a change from lower respiration frequencies to higher respiration frequencies by a step width between 0.1 bpm/2 s and 1 bpm/2 s, which leads to a faster weaning of the patient form the ventilator apparatus.

According to a further exemplary embodiment of the present invention, wherein in the method said optimization of said computed respiration frequency (f) is delayed in case of a change from lower respiration frequencies to higher respiration frequencies by a step width of 0.5 bpm/2 s, which is an ideal set-up for weaning the patient from the ventilator apparatus and a very high comfort for the patient.

According to an exemplary embodiment of the present invention, wherein in the method said optimization of said computed respiration frequency (f) is performed in case of a change from higher respiration frequencies to lower respiration frequencies without any delay, which leads to an additional enhancement of weaning of the patient from the ventilator apparatus and therefore to an increased comfort for the patient.

According to a further exemplary embodiment of the present invention, wherein in the method said optimization of said computed respiration frequency (f) is performed in case of a change from higher respiration frequencies to lower respiration frequencies without any delay and in case of a change from lower respiration frequencies to higher respiration frequencies is performed with a delay.

According to an exemplary embodiment of the present invention, a method for operating a ventilator in a ventilator apparatus, wherein in the method a duration ratio factor (D1) is set to a value of 0.36 in a computing system of the ventilator apparatus (step a); a duration ratio factor (D2) is set to a value of 0.5 in said computing system of the ventilator apparatus (step b); a patient's ideal body weight (IBW) and a percentage proximal minute volume (% Mvp) are determined (step c); at least one proximal minute volume (Mvp) is calculated with said percentage proximal minute volume (% Mvp) and the patient's ideal body weight (IBW) using said computing system (step d); at least one functional dead space volume (Vd) is determined using said computing system (step e); at least one time constant (R*C) is determined using said computing system (step f); a respiration frequency (f) is computed using said computing system, based on a previously defined linear lung model (ILM), comprising an assumed respiratory pressure (Rp_id), which follows a rectangular behavior, depending on said determined proximal minute volume (Mvp), said determined functional dead space (Vd), said determined time constant (R*C) and said set first ratio factor (D1), where said computed respiration frequency (f) is optimized on at least one minimum of the delivered mechanical respiration mean power ($\dot{W}$_tot), which is induced to the patient using at least one actuator of said ventilator (step g); an inspiratory time (TI) and an expiratory time (Te) are determined based on said computed respiration frequency (f) and based on said set second duration ratio factor (D2) using said computing system (step h); at least one tidal volume (Vt) is computed based on said previously computed respiration frequency (f) and said determined proximal minute volume (Mvp) using said computing system (step i); and at least a delivered respiratory pressure (Rp) of the ventilator is closed loop controlled based on the steps g) to i) (step j). Thereby, the respiratory pressure (Rp), delivered from said ventilator apparatus to the lung of the patient is optimized in an improved manner, while the tidal volume (Vt) is lowered and the respiration pressure (Rp) imposed to the lungs of the patient is lowered during a continuous ventilation of the patient.

After starting with step a) and step b), the sequence of step c) to step f) are ordered randomly, while the sequence of step g) to step i) are mandatory. This leads to a controlled operation of the ventilator, which finally ensures a protective ventilation of the patient's lung. According to an exemplary embodiment of the present invention, wherein in the method said steps c) to i) are repeated at least once and subsequently step j) is performed. Thereby, said computed respiration frequency (f) and said tidal volume (Vt) are determined more accurate, which results to an improved operation of the ventilator in the ventilator apparatus and furthermore leads to an enhanced ventilation of the lungs of the patient.

According to a further exemplary embodiment of the present invention, wherein in the method said computed respiration frequency (f) in step g), which is optimized on at least one minimum of the delivered mechanical respiration mean power ($\dot{W}$_tot), which is induced to the patient using at least one actuator of said ventilator, additionally depending on a positive end-expiratory pressure (PEEP). Therefore, the preferred working point of said at least one actuator of said ventilator will be reached more accurately.

According to an exemplary embodiment of the present invention, wherein in the method said positive end-expiratory pressure (PEEP), is a received input data of the computing system of the ventilator apparatus, which leads to a quick data processing and therefore to an enhanced artificial respiration of the patient.

According to a further exemplary embodiment of the present invention, wherein in the method said computed respiration frequency (f) is iteratively computed based on a fixed point iteration is computed with said computing system as:

$$f_{n+1} = \frac{Mvp}{4*Vd}\left(1 - \frac{D1}{f_n*R*C\left(e^{\frac{D1}{f_n*R*C}} - 1\right)}\right) + \frac{f_n}{2}, \quad (Eq.~7)$$

where Mvp is the proximal minute volume, Vd is the dead space, D1 is the first duration ratio factor and R*C is the time constant. This leads to a minimum delivered mechanical parameter, especial to a minimum delivered mechanical mean power, which is induced to the patient using said at least one actuator of said ventilator and is computed in a very accurate way.

According to a further exemplary embodiment of the present invention, wherein in the method said computed respiration frequency (f) is iteratively computed based on a Newton's method for finding roots with said computing system. This leads to a very quick determination of said respiration frequency.

According to another exemplary embodiment of the present invention, a ventilator apparatus is provided, comprising a ventilator with at least one actuator, further comprising at least one computing system connected to said at least one actuator of said ventilator; said at least one computing system comprising at least one memory and at least one processor; at least one transducer is configured to provide input signals from a patient to said at least one computing system including at least one minute volume (Mv); wherein said at least one processor is configured to execute a program stored in said memory; wherein said program computes a respiration frequency (f) based on a previously defined lung model (LM), depending on said at least one minute volume (Mv), at least one functional dead space (Vd), at least one time constant (R*C) and at least one duration ratio factor (D1, D2), which are stored in the memory; where said computed respiration frequency (f) is optimized on at least one minimum of a delivered respiration parameter (G_tot), which is induced to the patient using said ventilator; an inspiratory time (Ti) and an expiratory time (Te) based on said computed respiration frequency (f) and said at least one duration ratio factor (D1,D2) in said program; said program computes at least one tidal volume (Vt) based on said previously computed respiration frequency (f) and said determined minute volume (Mv); and a closed loop controller connected to the computing system, which is configured to provide output data representing a delivered respiration parameter of the ventilator including at least one of a respiratory pressure (Rp), a respiratory volume (Rv) and a respiratory flow (Rf), based on said computed respiration frequency (f), said inspiratory time (TI), said expiratory time (Te) and said tidal volume (Vt). Therefore, the respiration parameter, delivered from said ventilator to the lung of the patient is optimized, while the tidal volume (Vt) is lowered and the respiration pressure imposed to the lungs is lowered. Said ventilator apparatus, also called breathing apparatus, may also comprise more than one memory for storing one of the previous said parameters, while the at least one memory is either a digital memory or an analog memory.

According to a further embodiment of the present invention, wherein in the ventilator apparatus the said program is configured to compute a respiration frequency (f), which is optimized on at least one minimum of the delivered mechanical respiration mean power ($\dot{W}$_tot), which is induced to the patient using at least one actuator of said ventilator. This leads to an enhanced respiration of the patient's lung.

According to an embodiment of the present invention, wherein said ventilator further comprises a gas source, for example a turbine, for providing at least one of said delivered respiratory parameter, which is connected to said at least one actuator of said ventilator. Said at least one actuator of said ventilator is configured to control at least one of the delivered respiratory parameter from the ventilator to the patient using said computed respiration frequency (f). Therefore, said respiratory parameter is controllable very accurate and said tidal volume (Vt) is lowered, the respiration pressure imposed to the lungs is lowered and the delivered work is minimized.

According to a further embodiment of the present invention further comprises an external gas source, for example an external compressed gas source, for providing at least one of said delivered respiratory parameter, which is connected to said at least one actuator of said ventilator. Said at least one actuator of said ventilator is configured to control at least one of the delivered respiratory parameter from the ventilator to the patient using said computed respiration frequency (f). Said external pressure source ensures a stable air supply of said at least one actuator of said ventilator.

According to an embodiment of the present invention said at least one actuator of said ventilator comprises a valve. The valve ensures a quick and reliable control said at least one of the delivered respiratory parameter from the ventilator to the patient.

According to a further embodiment of the present invention, wherein in the ventilator apparatus the closed loop controller is a cascaded closed loop controller, wherein for example said tidal volume (Vt) is closed loop controlled in a first cascade and said delivering respiratory parameter, like the respiratory pressure (Rp), is closed loop controlled in a second cascade. This leads to an enhanced closed loop control of a respiratory parameter in a ventilation apparatus. Those skilled in art know comparable cascaded closed loop controller for said ventilator.

According to an embodiment of the present invention, wherein in the ventilator apparatus, said closed loop controller is a part of said computing system, which leads to a compact arrangement of said computing system.

According to a further embodiment of the present invention, wherein in the ventilator apparatus, said closed loop controller is separated from said computing system and connected to said computing system, which leads to an easy and cost saving arrangement of the components of the ventilator apparatus.

According to an exemplary embodiment of the present invention, wherein said ventilator apparatus further comprises a user interface coupled to said at least one computing system for setting at least one of the previous said parameters and further comprising a display unit coupled to said at least one computing system for displaying the output data, representing at least said computed respiration frequency (f) and at least one of said respiratory pressure (Rp) or said respiratory volume (Rv) or said respiratory flow (Rf). At least the important parameters are graphically displayable and therefore visible for medical professionals and/or other users. In addition, the user interface comprises at least one control instrument (Touchscreen, Keyport) to set at least one of the previously disclosed parameters. Said display unit is either part of said user interface or is separated from said user interface and connected to said user interface.

According to an exemplary embodiment of the present invention, wherein the ventilator apparatus comprises at least one transducer configured to provide input signals representing at least one of a positive end-expiratory pressure (PEEP), an oxygen concentration (FiO2), pressure limits (Pmax), an inspiration trigger (IT), an expiration trigger (ET), a carbon dioxide measurement data (DCO2), and a rise time. Therefore, an easy processing of the data in said at least one computing system is possible and an enhancement of the artificial respiration based on said input signals is ensured.

According to a further exemplary embodiment of the present invention, wherein in the ventilator apparatus comprises at least one A/D converter connected between said at least one transducer and said at least one computing system to convert analog signals from said at least one transducer into digital signals, which are processed in said at least one computing system, which leads to a fast processing of the signals.

According to an exemplary embodiment of the present invention, wherein in the ventilator apparatus comprises at least one D/A converter connected between said closed loop controller and said at least one actuator of said ventilator to convert the digital signals into analog signals and to supply said analog signals to said at least one actuator of said ventilator, which subsequently operates with at least said computed respiration frequency (f) and said tidal volume (Vt). This leads to an easy and fast processing of the signals and ensures an enhanced respiration of the patient.

Additional exemplary embodiments of the apparatus and the method of the invention are described below. Additional advantages result from the following description and figures.

BRIEF DESCRIPTION OF THE DRAWINGS

For the purpose of illustrating the invention, a presently preferred form of the invention is shown in the drawings. However, it is understood that this invention is not limited to the precise arrangements and instrumentalities shown.

DETAILED DESCRIPTION OF THE PREFERRED EMBODIMENTS

Figure 1:
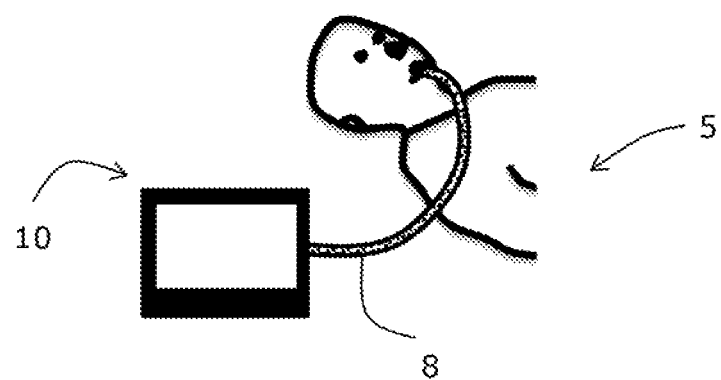
FIG. 1 depicts a general use case of a ventilator apparatus of the invention including a ventilation of a patient.

FIG. 1 depicts a ventilator apparatus 10, which is connected with a patient 5 using a respiratory tube 8, where the ventilator apparatus 10 is configured to ventilate a patient 5 according to the claimed method of the invention.

The present invention comprises a method for operating of a ventilator in a ventilator apparatus, which differs extensively from the known methods state of the art by its philosophy. The automatic ventilation modes state in the art uses the philosophy of Otis et. al, where the computed respiration frequency is based on the minimum work of human breathing. The present ventilation method, which is called adaptive ventilation mode (AVM), comprises a philosophy, where the iteratively computed respiration frequency is based on the minimum delivered parameter of the actuator of the ventilator induced to the patient's lungs. This extensive change in the way of thinking results in a new ventilation mode, which ensures a lung protective ventilation of mammals, especially of humans.

Figure 6:
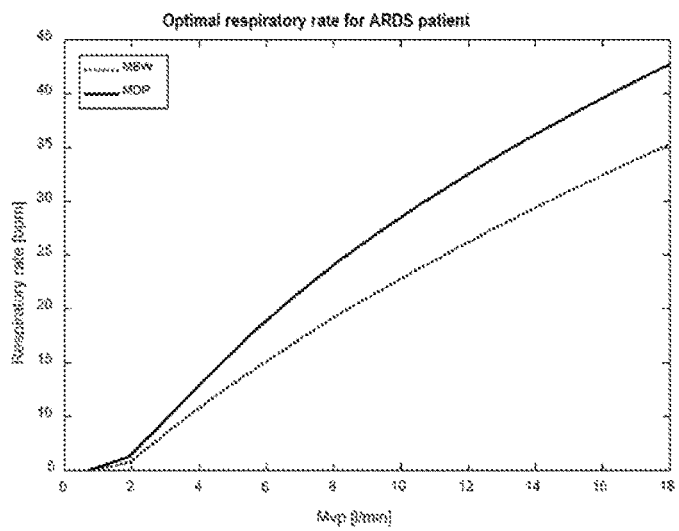
FIG. 6 depicts a diagram, which shows a comparison of the respiratory rate behavior of an ARDS patient using a respiration method following the minimum work of breathing (MBW) and an ARDS patient using a respiration method following the minimum delivered parameter of the actuator of the ventilator (MDP).
Figure 7:
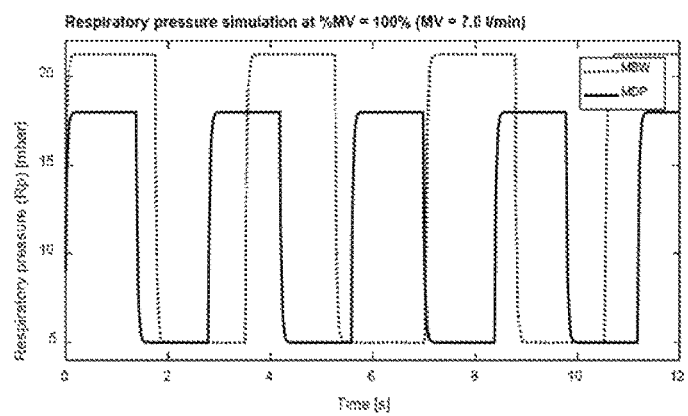
FIG. 7 depicts a diagram, which shows a comparison of the respiratory pressure behavior of an ARDS patient using a respiration method following the minimum work of breathing (MBW) and an ARDS patient using a respiration method (AVM) following the minimum delivered parameter of the actuator of the ventilator (MDP).
Figure 8:
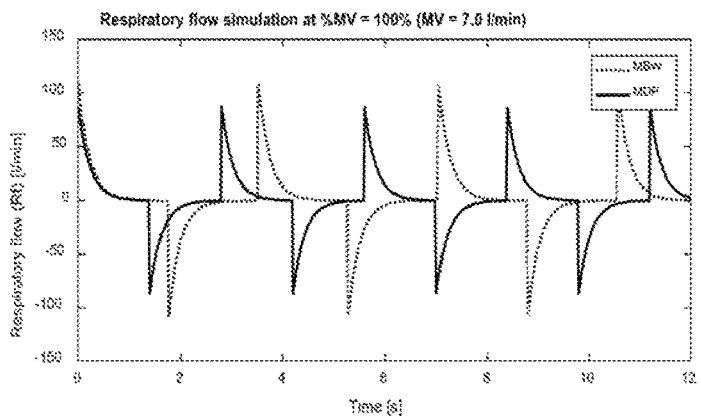
FIG. 8 depicts a diagram, which shows a comparison of the respiratory flow behavior of an ARDS patient using a respiration method following the minimum work of breathing (MBW) and an ARDS patient using a respiration method (AVM) following the minimum delivered parameter of the actuator of the ventilator (MDP).

FIG. 6 to FIG. 8 depict diagrams, which show a comparison of the respiratory parameter behavior of an ARDS patient, ventilated with a ventilator apparatus using a respiration method following the minimum work of breathing (MBW) (dotted line), and an ARDS patient ventilated with a ventilator apparatus using said respiration AVM method following the minimum delivered parameter of the actuator of the ventilator (MDP) (full line). The comparison assumes an ARDS patient with an ideal body weight (IBW) of 70 kg, a dead space (Vd) of 2.2 ml/kg, an airway resistance (R) of 9 mbar/l/s and a lung compliance of 25 ml/mbar.

The diagram in FIG. 6 depicts at its ordinate a respiratory rate [bpm] and at the abscissa a proximal minute volume [l/min]. Said respiratory rate is calculated by a respiration frequency (f) multiplied by 60. The diagram clearly shows an increased slope of the respiratory rate with respect to an increasing proximal minute volume using the AVM method for the operation of the ventilator in a ventilator apparatus, which is favourable for a protective respiration of a patient's lung.

The diagram in FIG. 7 depicts at its ordinate a respiratory pressure [mbar] and at the abscissa the time [s]. The diagram shows a decreased respiratory pressure with respect to the time [s] using the AVM method (full line) with the MDP mode, while the amount of respiration cycles is increased compared to said MBW mode. Therefore, a decreased stress of the patient's lung is ensured. The same behavior is observed in FIG. 8 with the respiratory flow [l/min] at its ordinate.

Figure 2:
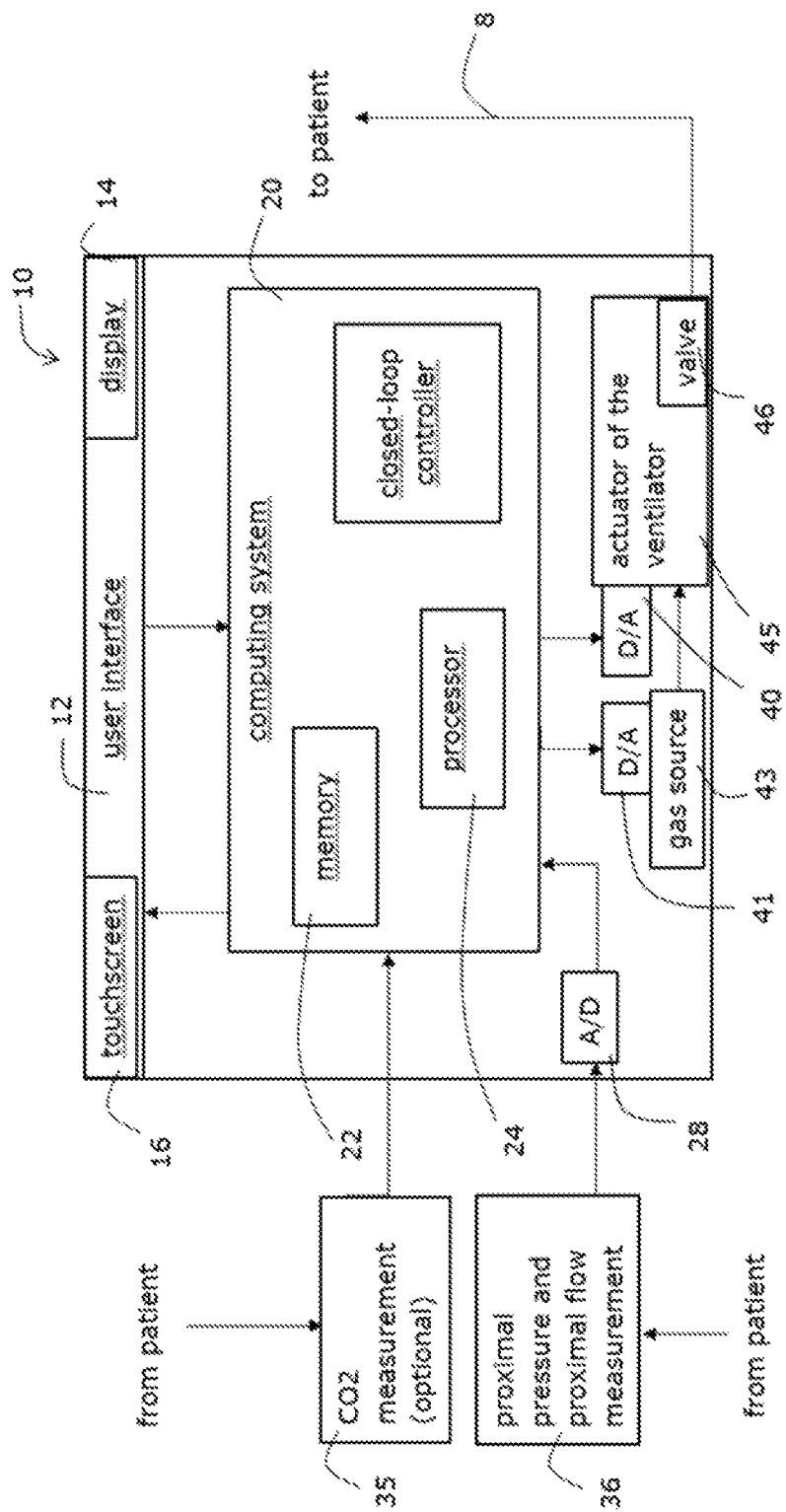
FIG. 2 is a block diagram depicting general components of the invention including amongst other things a ventilator apparatus, a user interface, a computing system, an actuator of a ventilator and transducers.

FIG. 2 depicts a block diagram with the general components and applications of the ventilation apparatus 10 of the invention using the AVM method to improve the operation of the at least one actuator of the said ventilator in said ventilation apparatus. Said ventilation apparatus 10 comprises a user interface 12 connected to a display unit 14. Said user interface 12 comprises a touchscreen 16 with which the user is able to enter a data, e.g. a patient data like among others the ideal body weight (IBW) of the patient. A computing system 20 of said ventilation apparatus 10 comprises a memory 22 and a processor 24, where a program comprising at least the method of the invention is executed by said processor 24. The received data are saved in said memory 22 or are computed directly in said processor 24. Said ventilator apparatus 10 further comprises a A/D converter 28 connected to said computing system 20. Transducers 35, 36 provide at least one input signal, e.g. a proximal respiration pressure (Rpp), a proximal respiration flow (Rfp) and a carbon dioxide data (DCO2), concerning to the patient's data and are connected to said A/D converter 28 or are directly connected to said computing system 20. Said computing system 20 further comprises a closed-loop controller 30. Said closed-loop controller 30 is further connected via a D/A converter 40 with an actuator of the ventilator 45, which ensures the ventilation of a patient. Said ventilator apparatus 10 comprises a gas source 43, which is connected via a D/A converter 41 to said closed loop controller 30. Said gas source 43 is configured to generate a mechanical respiration mean power and is connected to said at least one actuator 45. Said gas source 43 is for example a turbine or an external compressed a gas source and is configured to supply said at least one actuator of said ventilator 45 with compressed gas, like among others are air or oxygen. Said ventilator comprises at least said one actuator 45 or comprises at least said gas source 43 and at least said one actuator 45. Said at least one actuator 45 comprises a valve 46 for controlling the mechanical respiration mean power, which is delivered to the patient 5, while additionally losses in the respiratory tube 8 are considered.

Figure 3:
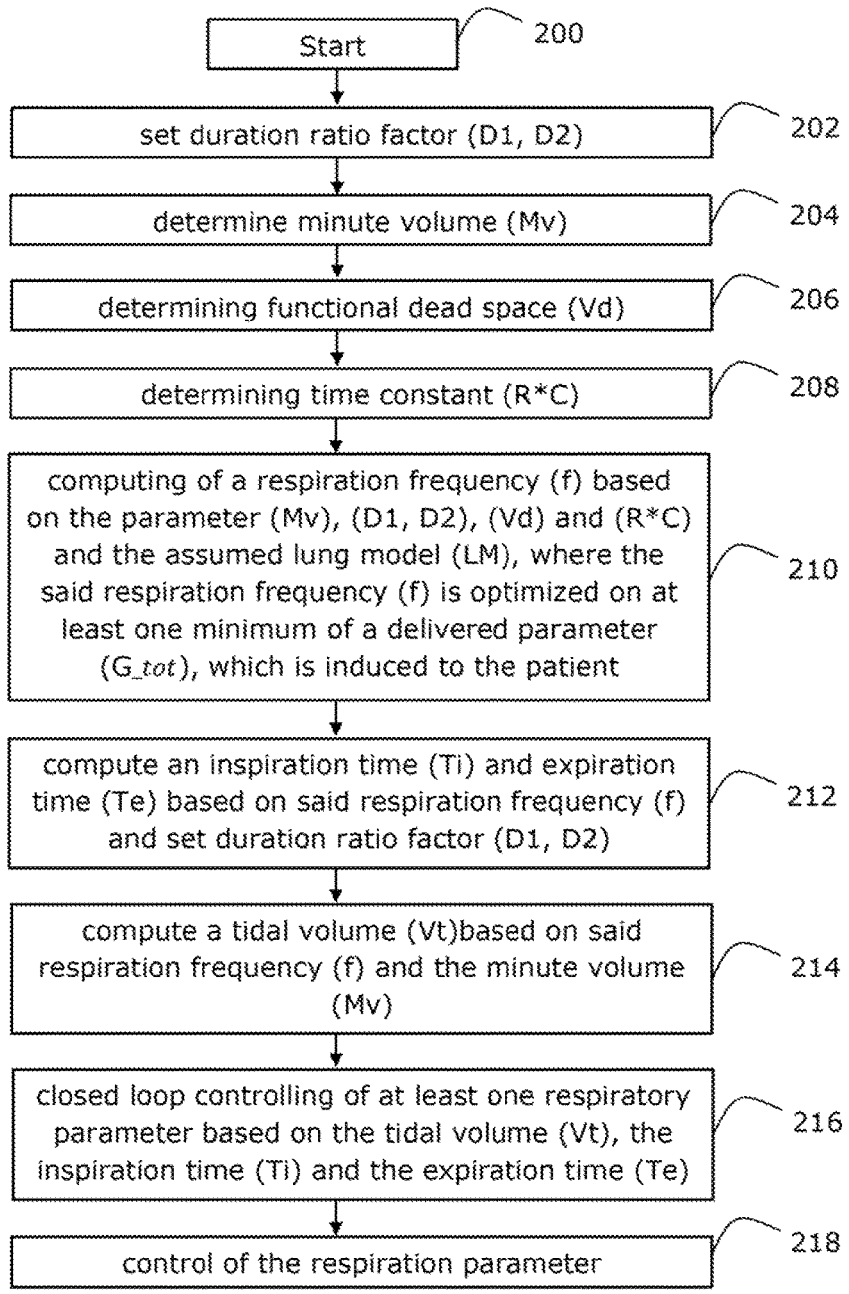
FIG. 3 is a process flow chart illustrating one embodiment of a method according to the invention, including a general sequence of steps executable by a programmable computing system of the invention.

FIG. 3 shows a process flow chart of one embodiment of a general sequence of steps executed to carry out said AVM method of the invention to improve the operation of at least one actuator of a ventilator in a ventilator apparatus. After the start of the flow chart 200, a duration ratio factor (D1, D2) is set in said computing system of said ventilator apparatus in step 202, where the value of the duration ratio factor (D1, D2) is experimentally defined by an inspiration-to-expiration ratio, which is known by those skilled in art and limited in a range of 1:4 to 1:1.

In the next step 204 a minute volume (Mv) is determined in said computing system, which is either the proximal minute volume (Mvp) or the alveolar minute volume (Mva).

In the next step 206 a functional dead space (Vd) is determined in said computing system, followed by the next step 208 which comprises a determination of a time constant (R*C) in said computing system based on the continuously measured proximal respiration flow (Rfp) data.

After the general data collection disclosed in the steps 202 to 208, the respiration frequency (f) is iteratively computed using said computing system in the step 210. Said iteratively computed respiration frequency (f) is based on a lung model (LM) and depends on said determined minute volume (Mv), said determined functional dead space (Vd), said determined time constant (R*C) and said set duration ratio factor (D1, D2), where said computed respiration frequency (f) is optimized on at least one minimum of the delivered respiration parameter (G_tot), which is induced to the patient using said ventilator.

In the next step 212, the inspiration time (Ti) and the expiration time (Te) are computed using said computing system based on set duration ratio factor (D1, D2) and said computed respiration frequency (f) of step 210.

After the step 212, the program passes the step 214, where the tidal volume (Vt) is estimated using said computing system based on one of said computed respiration frequencies (f) and said determined minute volume (Mv) of step 204.

In the subsequent step 216, a closed loop control of at least one respiration parameter is initiated based on the estimated tidal volume (Vt), the computed inspiration time (Ti) and the computed expiration time (Te) using a closed loop controller.

The final step 218 in the flow chart comprises the control of the respiratory parameter sent from the actuator of the ventilator to the patient. Those skilled in art know, that there is also a control of the other respiratory parameters possible, like the respiratory flow (Rf).

The previous said lung model (LM) is either a linear lung model (lLM) or a nonlinear lung model (nLM). A linear lung model comprises at least a linear behavior of the airway Resistance (R) and at least a linear behavior of the lung compliance (C). Said nonlinear lung model (nLM) comprises an airway resistance (R) with a linear behavior (Ra) and a quadratic behavior (Ra'), while the behavior of the lung compliance (C) is linear. Other behaviors of the airway Resistance (R), e.g. a polynomial behavior, are also possible.

The basis of said lung model (LM) are the equation of motion, which are known from literature, and are calculated as $$P(t) = \frac{V(t)}{C} + R * F(t), \quad \text{(Eq. 8)}$$

for the linear lung model (lLM) and $$P(t) = \frac{V(t)}{C} + Ra * F(t) + Ra' * F(t)^2, \quad \text{(Eq. 9)}$$

for the nonlinear lung model (nLM), where P(t) is the actual proximal pressure, V(t) is the actual lung volume and F(t) is the actual flow to the patient.

In the preferred embodiment, the assumed respiratory pressure (Rp_id) follows a rectangular behavior, while the assumed respiratory flow (Rf_id) follows an exponential behavior.

Considering the previous assumption, the delivered respiration parameter (G_tot) of the ventilator is expressed by:

$$G_{tot} = G_C + G_R, \quad \text{(Eq. 10)}$$

where $G_C$ is the considered part of the lung compliance (C) and $G_R$ is the assumed part of the airway resistance (R) of the patient.

Said computed respiration frequency (f) is optimized on at least one minimum of the delivered respiration parameter (G_tot) which is induced to a patient using said ventilator:

$$g(f) = \frac{dG_{tot}}{df} = 0 \quad \text{(Eq. 11)}$$

The respiration frequency (f) is generally computed in said computing system by the following steps:

1. $Mva(0) = Mvp - f \cdot V_d;$ (Eq. 12)

2. $n = 0$ (Eq. 13)

3. $f = \underset{f_{min} < f_x < f_{max}}{\operatorname{argmin}} (G_{tot}(Mva(n), f_x))$ (Eq. 14)

4. $Mva(n+1) = k \cdot (Mvp - f \cdot V_d) + (1-k) \cdot Mva(n)$ (Eq. 15)

5. $n = n + 1$ (Eq. 16)

6. Go to Step 3 if $|Mva(n) - Mva(n-1)| > \epsilon,$ (Eq. 17)

where k<1 is suitable for convergence, $f_{min}$ is the minimal tolerable respiration frequency, $f_{max}$ is the maximal tolerable respiration frequency and $\epsilon$ is the criteria for successful convergence. Those skilled in art knows how to write the above disclosed equations into a program code using for example a C++® software package, C#® software package or similar software packages.

Figure 4:
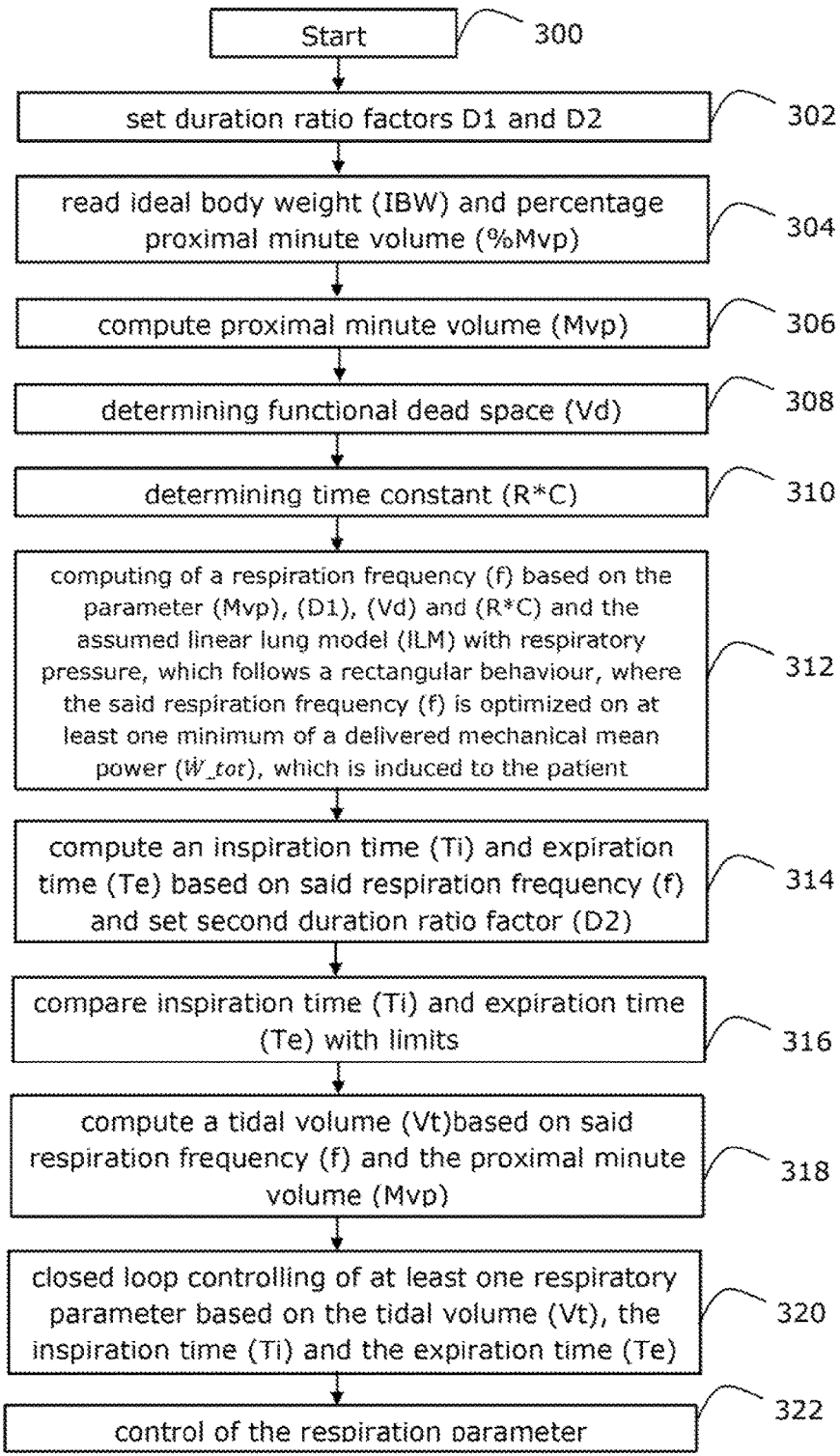
FIG. 4 is a process flow chart illustrating one preferred embodiment of a method according to the invention, including a preferred sequence of steps executable by a computing system of the invention.

FIG. 4 shows a process flow chart of one embodiment of a preferred sequence of steps executed to carry out said AVM method of the invention to operate at least one actuator of a ventilator in said ventilator apparatus in a very detailed manner. Those skilled in art know, that there will be sent an alarm signal from the ventilator apparatus, if one of the following parameters are run out of their limits.

After the start of the flow chart 300, a first duration ratio factor (D1) is set to a value of 0.36 in a computing system of the ventilator apparatus, which is an experimental value, defined by field tests of the AVM mode. In the same step 302 a second duration ratio factor (D2) is set to a value of 0.5 in said computing system, which results of an inspiration-to-expiration ratio (I:E) of 1:1.

At step 304 the percentage proximal minute volume (% Mvp), the patient's ideal body weight (IBW) are determined, provided as input parameter in a user interface.

In the next step 306 the proximal minute volume (Mvp) based on the patient's ideal body weight (IBW) and the percentage proximal minute volume (% Mvp) is computed in said computing system.

In the next step 308 a functional dead space (Vd) is determined in said computing system, which is either calculated by said patient's ideal body weight (IBW) and multiplied by the usually used factor of 2.2 ml/kg, or which can be estimated considering a carbon dioxide measurement data.

The next step 310 comprises the determination of a time constant (R*C) in said computing system based on the continuously measured proximal respiratory flow (Rfp) data of the patient.

After the general data collection disclosed in the steps 302 to 310, the respiration frequency (f) is iteratively computed using said computing system in the step 312. The iteratively computed respiration frequency (f) is based on the previously disclosed assumed linear lung model (ILM) (Eq. 8) with a respiratory pressure, which follows a rectangular behavior and depends on the determined proximal minute volume (Mvp), said determined functional dead space (Vd), said determined time constant (R*C) and said set first duration ratio factor (D1), where said computed respiration frequency (f) is optimized on at least one minimum of the delivered mechanical respiration mean power ($\dot{W}\_tot$), which is induced to the patient using said at least one actuator of the ventilator, which is explained subsequently in detail.

Assuming a respiratory pressure (Rp_id) follows a rectangular behavior, while an assumed respiratory flow (Rf_id) follows an exponential behavior.

Considering the previous assumption, the delivered mechanical respiration mean power ($\dot{W}\_tot$) of said actuator of the ventilator is expressed by:

$$\dot{W}_{tot} = \dot{W}_C + \dot{W}_R, \qquad \text{(Eq. 18)}$$

where $\dot{W}_C$ is the part of the power considering the lung compliance (C) and $\dot{W}_R$ is the part of the power considering the airway resistance (R) of the patient.

The disclosed lung compliance part $\dot{W}_C$ is determined by $$\dot{W}_c = \frac{1}{2 \cdot C} \cdot f \cdot V_t^2, \qquad \text{(Eq. 19)}$$

and the disclosed airway resistance part $\dot{W}_R$ is determined by $$\dot{W}_R = \frac{1}{2 \cdot C} \cdot f \cdot V_t^2 \cdot \coth\left(\frac{Ti}{2 \cdot R \cdot C}\right), \qquad \text{(Eq. 20)}$$

where C is said lung compliance, R*C is said time constant, Ti is said inspiration time and $V_t$ is the tidal volume, which can be expressed by $$V_t = \frac{Mva}{f} + V_d, \qquad \text{(Eq. 21)}$$

where Mva is the alveolar minute volume and Vd is the functional dead space.

Said computed respiration frequency (f) is optimized on at least one minimum of the delivered mechanical respiration mean power ($\dot{W}\_tot$), which is induced to a patient using said actuator of said ventilator:

$$g(f) = \frac{dW_{tot}}{df} = 0, \qquad \text{(Eq. 22)}$$

Considering the known substitution of Mva=Mvp−Vd*f, the resulting iteratively computed respiration frequency (f) based on a fixed point iteration is computed with said computing system as:

$$f_{n+1} = \frac{Mvp}{4 * Vd}\left(1 - \frac{D1}{f_n * R * C\left(e^{\frac{D1}{f_n * R * C}} - 1\right)}\right) + \frac{f_n}{2}, \qquad \text{(Eq. 23)}$$

In the next step 314, the inspiration time (Ti) and the expiration time (Te) are computed in said computing system based on determined second duration ratio factor (D2) and the computed respiration frequency (f) of step 312.

After the step 314, the program passes the step 316, where the previously computed inspiration time (Ti) and the computed expiration time (Te) is limited by an extremum explained in equations Eq. 4 to Eq. 6.

In the next step 318, the tidal volume (Vt) is estimated in said computing system based on one of the previously computed respiration frequency (f) and the determined proximal minute volume (Mvp) of the step 304.

In subsequent step 320, a closed loop control is initiated based on the estimated tidal volume (Vt), the computed inspiration time (Ti) and the computed expiration time (Te) using the closed loop controller.

The final step 322 in the flow chart comprises the control of a respiration parameter, in particular the respiratory pressure (Rp), sent from said at least one actuator of the ventilator to the patient.

A further assumption of the delivered mechanical respiration mean power ($\dot{W}\_tot$), which is induced to a patient using said actuator of the ventilator comprising additionally a $\dot{W}_{PEEP}$ and is expressed by:

$$\dot{W}_{tot} = \dot{W}_C + \dot{W}_R + \dot{W}_{PEEP}, \qquad \text{(Eq. 24)}$$

where $\dot{W}_{PEEP}$, is the assumed part considering the positive end-expiratory pressure (PEEP) of the patient. In this case, a positive end-expiratory pressure (PEEP) of the patient larger than 0 is considered, where $\dot{W}_{PEEP}$ is expressed by $$\dot{W}_{PEEP} = f \cdot \text{PEEP} \cdot V_t. \qquad \text{(Eq. 25)}$$

In addition, an intrinsic PEEP exists in the human lung, which is not measurable but can be calculated analytically. For proper computation, the effective PEEP in the lung is used. In respect to an intrinsic PEEP, not only the PEEP setting of the ventilation is considered, but also the intrinsic PEEP of the patient. Therefore, the PEEP in the lung is given by:

$$PEEP = PEEP_{Set} + PEEP_{intr}, \quad (Eq. 26)$$

The respiration frequency (f) in the previously disclosed step 210 or step 312 is alternatively iteratively computed in said computing system by the following steps:

1. $Mva(0) = Mvp - f \cdot V_d;$ (Eq. 27)

2. $n = 0$ (Eq. 28)

3. $f = \underset{f_{min} < f_x < f_{max}}{\operatorname{argmin}} (\dot{W}_{tot}(Mva(n), f_x))$ (Eq. 29)

4. $Mva(n+1) = k \cdot (Mvp - f \cdot V_d) + (1-k) \cdot Mva(n)$ (Eq. 30)

5. $n = n + 1$ (Eq. 31)

6. Go to Step 3 if $|Mva(n) - Mva(n-1)| > \epsilon,$ (Eq. 32)

where k<1 is suitable for convergence, $f_{min}$ is the minimal tolerable respiration frequency, $f_{max}$ is the maximal tolerable respiration frequency and $\epsilon$ is the criteria for successful convergence. Those skilled in art knows how to write the above disclosed equations into a program code using for example a VISUAL C++® software package, C#® software package or similar software packages.

In addition, the previously disclosed new adaptive ventilation mode (AVM) is combinable with other ventilation modes, which are known from the state of the art. One possible combination of the previously mentioned adaptive support ventilation (ASV)-like mode, which is based on the ventilation philosophy of Otis et. al, is depicted FIG. 5.

Figure 5:
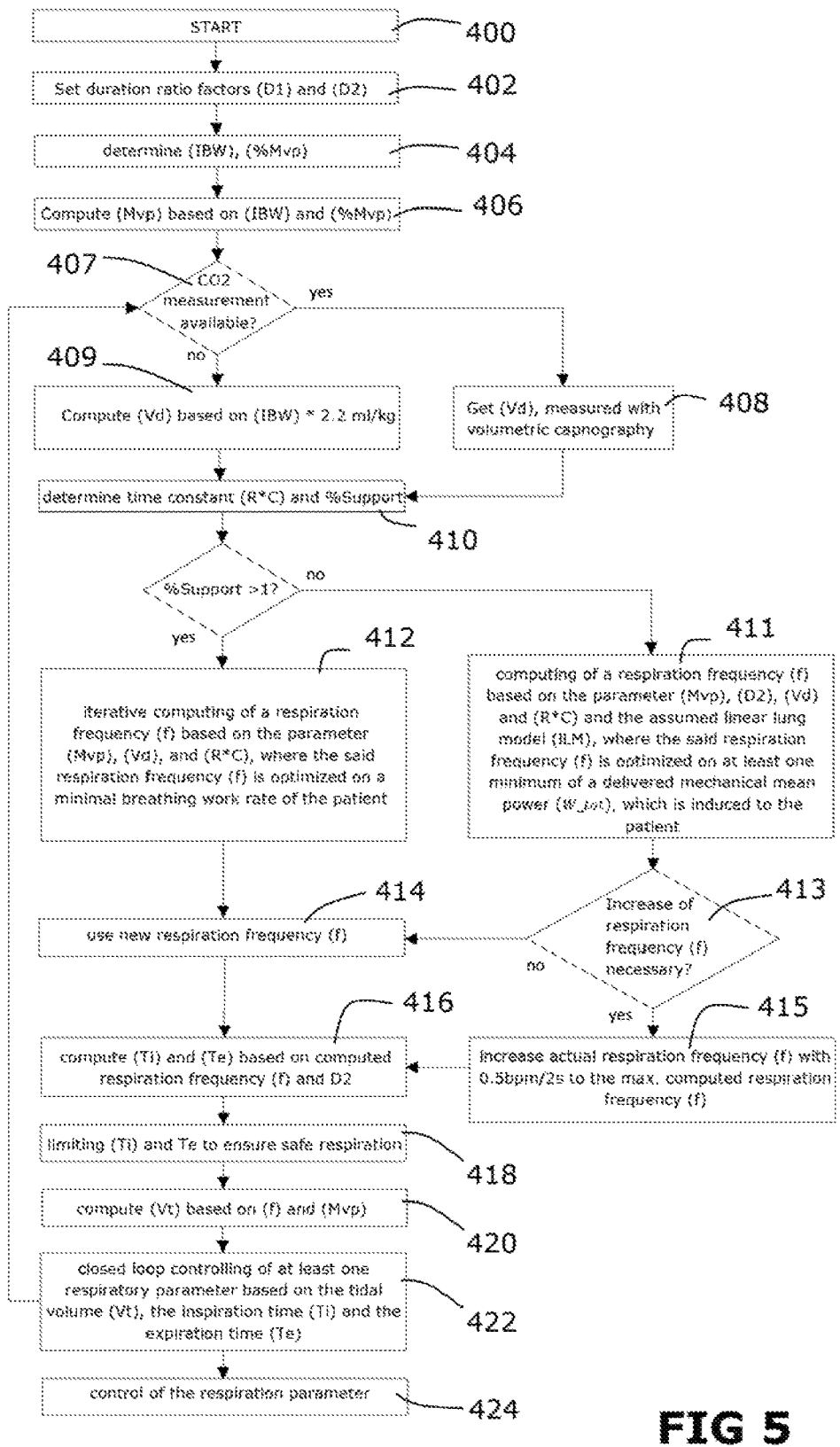
FIG. 5 is a process flow chart illustrating further embodiment of a method according to the new respiration method of the invention combined with a known ventilation method, including a preferred sequence of steps executable by a computing system of the invention.

FIG. 5 shows a process flow chart of one embodiment of a preferred sequence of steps executed to carry out the AVM method of the invention in combination with the adaptive support ventilation (ASV)-like mode to further improve the operation of a ventilator in a ventilator apparatus. After the start of the flow chart 400 a first duration ratio factor (D1) and a second duration ratio factor (D2) is provided in the computing system, which are experimentally defined values, where the value of the first duration ratio factor (D1) is set to 0.36 and the value of the second duration ratio factor (D2) is set to 0.5 (step 402).

At step 404 the percentage proximal minute volume (% Mvp), the patient's ideal body weight (IBW) are determined and provided to said computing system.

In the next step 406 the proximal minute volume (Mvp) based on the patient's ideal body weight (IBW) and the percentage proximal minute volume (% Mvp) is computed in said computing system.

Alternatively, the proximal minute volume (Mvp) is read directly in step 404 or the alveolar minute volume (Mva) is used.

In the next step 407, a possibly measured carbon dioxide data (DCO2) is checked and if the measurement is provided, a real functional dead space (Vd) is computed in said computing system considering the volumetric capnography (step 408). The volumetric capnography is usually measured with the carbon dioxide data (DCO2) and the proximal respiratory flow measurement (Rfp). Those skilled in art also know other measurement techniques to provide the carbon dioxide data (DCO2).

If the measured carbon dioxide data (DCO2) is not provided by a measurement technique, the functional dead space (Vd) is computed in said computing system by the patient's ideal body weight (IBW) multiplied by the usually used factor of 2.2 ml/kg, which is shown in step 409. At step 410, the time constant (R*C) and the percentage of spontaneous breaths of the patient (% Support) is measured by a proximal pressure and proximal flow measurement with a transducer of the ventilator apparatus In this preferred embodiment, if the percentage of spontaneous breaths of the patient (% Support) is smaller than 1, the ventilation AVM method of this invention is performed, which is disclosed in step 411. There the respiration frequency (f) is iteratively computed in said computing system, which is based on a previously disclosed linear lung model (ILM) and depends on said determined proximal minute volume (Mvp), said determined functional dead space (Vd), said determined time constant (R*C) and said set first duration ratio factor (D1), where said computed respiration frequency (f) is optimized on at least one minimum of the delivered mechanical respiration mean power ($\dot{W}$_tot), which is induced to a patient using said actuator of the ventilator.

After step 411, said computed respiration frequency (f) is compared to the actual respiration frequency (f) of the patient and if necessary (step 413), the actual induced respiration frequency (f) is slowly increased with step width of 0.5 bpm/2 s using said computing system, which is depicted in step 415. However, the increase of the actual induced respiration frequency is limited by the computed respiration frequency (f) of step 411. Otherwise the new said computed respiration frequency (f) in said computing system is used immediately, shown in step 414.

If the previous said percentage of spontaneous breaths of the patient (% Support) is larger than 1, the ASV-like mode is performed, which is disclosed in step 412. There the respiration frequency (f) is iteratively computed in said computing system, which depends on the determined proximal minute volume (Mvp), the determined functional dead space (Vd), the determined time constant (R*C), where said computed respiration frequency (f) is optimized on minimum breathing work frequency (f) of the patient and used immediately for the computations in said computing system in the next step 416.

In the next step 416, the inspiration time (Ti) and the expiration time (Te) are computed in said computing system based on said set second duration ratio factor (D2) and either with the computed respiration frequency (f) in step 411 or with the computed respiration frequency (f) in step 412.

In the next step 418, the previously computed inspiration time (Ti) and the computed expiration time (Te) is limited, explained by the equations Eq. 4 and Eq. 5, while the expiration time (Te) is limited with a maximum value of 12 seconds.

After the step 418, the program passes the step 420, where tidal volume (Vt) is estimated in said computing system based on one of the previously computed respiration frequencies (f) disclosed in the steps 414 or 415 and the computed proximal minute volume (Mvp) of the step 406.

In subsequent step 420, a closed loop control is initiated based on the estimated tidal volume (Vt), the computed inspiration time (Ti) and the computed expiration time (Te) using a closed loop controller and starting again with the check of the possibly carbon dioxide measurement of step 407.

The final step 424 in the flow chart comprises the control of the respiratory pressure sent from the actuator of the ventilator to the patient.

LIST OF REFERENCE SIGNS 5 patient
8 respiratory tube
10 ventilation apparatus
12 user interface
14 display unit
16 touchscreen
20 computing system
22 memory
24 processor
28 A/D converter
35 transducer (CO2 measurement)
36 transducer proximal pressure and flow measurement
40 D/A converter
41 D/A converter
43 gas source
45 actuator of the ventilator
46 valve
200-218 general sequence of steps of the invention
300-322 one embodiment of sequence of steps of the invention
400-424 alternative embodiment of sequence of steps of the invention
Mva alveolar minute volume
Vta alveolar tidal volume
Mv minute volume
Vd dead space
R*C time constant
D1 first duration ratio factor
D2 second duration ratio factor
LM lung model
lLM linear lung model
nLM nonlinear lung model
f respiration frequency
G_tot delivered parameter of the ventilator
    W_tot delivered mechanical respiration work of the actuator of the ventilator
    $\dot{W}$_tot delivered mechanical respiration mean power of the actuator of the ventilator
Ti inspiration time
Te expiration time
Vt tidal volume
Rp respiratory pressure
Rf respiratory flow
Rv respiratory volume
R airway resistance
Ra linear part of the airway resistance
Ra' quadratic part of the airway resistance
C lung compliance
Rp_id ideal respiratory pressure
Rf_id ideal respiratory flow
Rv_id ideal respiratory volume
Mvp proximal minute volume
IBW ideal body weight
% Mvp percentage proximal minute volume
PEEP positive end-expiratory pressure
I:E inspiration-to-expiration ratio
$Ti_{max\_IBW}$ maximum inspiration time based on the ideal body weight
$Ti_{max}$ maximum inspiration time
$PEEP_{intr}$ upper limit for the Intrinsic positive end-expiratory pressure
% Support percentage of spontaneous breaths of the patient
ASV adaptive support ventilation
AVM adaptive ventilation mode
Rpp proximal respiration pressure
Rfp proximal respiration flow
DCO2 carbon dioxide data
P(t) actual proximal pressure
F(t) actual proximal flow
V(t) actual lung volume

The invention claimed is:

1. A method for operating a ventilator in a ventilator apparatus comprising the steps of:
    a) setting at least one duration ratio factor (D1, D2) in a computing system of the ventilator apparatus;
    b) determining at least one minute volume (Mv) using said computing system;
    c) determining at least one functional dead space (Vd) using said computing system;
    d) determining at least one time constant (R*C) using said computing system;
    e) computing a respiration frequency (f) using said computing system, based on a previously defined lung model (LM), depending on said determined minute volume (Mv), said determined functional dead space (Vd), said determined time constant (R*C) and said set duration ratio factor (D1, D2), where said computed respiration frequency (f) is optimized on at least one minimum of a delivered parameter (G_tot), which is induced to a patient using said ventilator;
    f) determining an inspiratory time (Ti) and an expiratory time (Te) based on said computed respiration frequency (f) and said set duration ratio factor (D1, D2) using said computing system;
    g) computing at least one tidal volume (Vt) based on said computed respiration frequency (f) and said determined minute volume (Mv) using said computing system; and
    h) closed loop controlling at least one of a delivered respiratory parameter of the ventilator including at least one of a respiratory pressure (Rp), a respiratory flow (Rf) or a respiratory volume (Rv) of the ventilator based on the steps e) to g).

2. The method of claim 1, wherein step b) to step g) are repeated at least once and subsequently step h) is performed.

3. The method of claim 1, wherein said at least one minimum of a delivered parameter (G_tot) includes at least one minimum of the delivered mechanical respiration mean power ($\dot{W}$_tot), which is induced to the patient using at least one actuator of said ventilator.

4. The method of claim 1, wherein said lung model (LM) in step e) comprises an airway resistance (R) and a lung compliance (C), which following independently at least a linear behaviour or at least a quadratic behaviour or at least a polynomial behaviour.

5. The method of claim 1, wherein said lung model (LM) in step e) further comprises at least one of the group of an assumed respiratory pressure (Rp_id), an assumed respiratory flow (Rf_id) and an assumed respiratory volume (Rv_id), which following at least a of an exponential behaviour, a rectangular behaviour, a sinusoidal behaviour or a saw tooth behaviour.

6. The method of claim 1, wherein said minute volume (Mv) in step b) is the proximal minute volume (Mvp) calculated based on a previously determined patient's ideal body weight (IBW) and a previously determined percentage proximal minute volume (% Mvp) or is the alveolar minute volume (Mva).

7. The method of claim 1, wherein said computed respiration frequency (f) in step e), which is optimized on at least one minimum of a delivered parameter (G_tot), which is induced to the patient using said ventilator, additionally depends on a positive end-expiratory pressure (PEEP).

8. The method of claim 7, wherein said positive end-expiratory pressure (PEEP), is a received input data of said computing system.

9. The method of claim 1, wherein said determined functional dead space (Vd) is determined based on volumetric capnography, which is measured with a carbon dioxide measurement and a proximal flow measurement.

10. The method of claim 1, wherein said computed respiration frequency (f) in step e) is optimized on at least one minimum of the delivered mechanical respiration work (W_tot), which is induced to the patient using at least one actuator of said ventilator.

11. The method of claim 1, wherein a set first duration ratio factor (D1) in step a) is computed with said computing system by:

$$D1 = \frac{I:E}{(1+I:E)};$$

where I:E is the inspiration-to-expiration ratio and said first duration ratio factor (D1) is used for computing of the respiration frequency (f) in step e);
or wherein a set first duration ratio factor (D1) in step a) is set to a value between 0.5 and 0.3 and is used for computing of the respiration frequency (f) in step e).

12. The method of claim 1, wherein a set first duration ratio factor (D1) in step a) is set to a value of 0.5 and is used for computing of the respiration frequency (f) in step e).

13. The method of claim 1, wherein a second duration ratio factor (D2), which is additionally set in step a) is used to determine said inspiration time (Ti) and said expiration time (Te) in step f) and is unequal to said first duration ratio factor (D1),
or wherein a second duration ratio factor (D2), which is additionally set in step a) is used to determine said inspiration time (Ti) and said expiration time (Te) in step f) and is determined by an assumed inspiration-to-expiration (I:E) ratio.

14. The method of claim 1, wherein a second duration ratio factor (D2), which is additionally set in step a) is used to determine said inspiration time (Ti) and said expiration time (Te) in step f) and is set to a value of 0.5.

15. The method of claim 1, wherein the inspiration time (Ti) is limited by an extremum preferably a minimum value computed with said computing system as:

max(R*C, 0,5s), and/or depending on a maximum value computed with said computing system as:

max(Ti$_{max\_IBW}$, min(Ti$_{max}$, 3*R*C)), where Ti$_{max\_IBW}$ is a maximum inspiration time based on the ideal body weight (IBW) of the patient, which comprises a range of 1 second to 3 seconds, Ti$_{max}$ is a maximum inspiration time, which comprises a range of 2 seconds and 3 seconds and R*C is the time constant in seconds.

16. The method of claim 1, wherein step d) further comprises determining at least one lung compliance (C) using said computing system.

17. The method of claim 16, wherein said expiration time (Te) is limited by an extremum, in particular a minimum value computed with said computing system as:

$$R*C*\max\left(2, \ln\left(\frac{Vt}{C*PEEP_{intr}}+1\right)\right),$$

where R*C is the time constant in seconds, Vt is the tidal volume, PEEP$_{intr}$ is the upper limit for the intrinsic positive end-expiratory pressure, which is set preferably to 1.5 mbar, and C is the lung compliance.

18. The method of claim 1, wherein said expiration time (Te) is limited with a maximum value less than 13 seconds.

19. The method of claim 1, wherein after the step d) a percentage of spontaneous breaths of a patient (% Support) is determined by a proximal pressure and a proximal flow measured with at least one transducer of said ventilator apparatus.

20. The method of claim 19, wherein said computed respiration frequency (f) is further optimized based on said determined percentage of spontaneous breaths of the patient (% Support) using said computing system.

21. The method of claim 20, wherein said optimization of said computed respiration frequency (f) is delayed in case of a change from lower respiration frequencies to higher respiration frequencies, or
said optimization of said computed respiration frequency (f) is performed in case of a change from higher respiration frequencies to lower respiration frequencies without any delay.

22. The method of claim 21, wherein said optimization of said computed respiration frequency (f) is delayed by a step width between 0.1 bpm/2 s and 1 bpm/2 s, in particular delayed by a step width of 0.5 bpm/2 s.

* * * * *